(12) United States Patent
Crainich (10) Patent No.: US 8,574,271 B2
(45) Date of Patent: Nov. 5, 2013

(54) FIXATION PLATE SCREW RETENTION

(75) Inventor: Lawrence Crainich, Charlestown, NH (US)

(73) Assignee: Paul Andrew Glazer, Chestnut Hill, MA (US)

( * ) Notice: Subject to any disclaimer, the term of this patent is extended or adjusted under 35 U.S.C. 154(b) by 449 days.

(21) Appl. No.: 12/846,570

(22) Filed: Jul. 29, 2010

(65) Prior Publication Data

US 2011/0029024 A1 Feb. 3, 2011

Related U.S. Application Data

(60) Provisional application No. 61/229,525, filed on Jul. 29, 2009.

(51) Int. Cl.
*A61B 17/80* (2006.01)

(52) U.S. Cl.
USPC .............. 606/290; 606/289; 606/70; 606/71; 411/353; 411/533; 411/970

(58) Field of Classification Search
USPC ............... 606/70–71, 280–299, 920–906; 411/353, 533, 970, 999
See application file for complete search history.

(56) References Cited

U.S. PATENT DOCUMENTS

| | | | | |
|---|---|---|---|---|
| 4,911,726 A | * | 3/1990 | Warkentin | 81/124.2 |
| 5,364,399 A | | 11/1994 | Lowery et al. | |
| 5,578,034 A | * | 11/1996 | Estes | 606/281 |
| 5,931,838 A | * | 8/1999 | Vito | 606/281 |
| 5,954,722 A | | 9/1999 | Bono | |
| 6,193,721 B1 | | 2/2001 | Michelson | |
| 6,402,755 B1 | * | 6/2002 | Pisharodi | 606/71 |
| 6,637,993 B2 | * | 10/2003 | Murakami | 411/120 |
| 7,001,389 B1 | * | 2/2006 | Navarro et al. | 606/71 |
| 7,247,157 B2 | * | 7/2007 | Prager et al. | 606/64 |
| 7,309,340 B2 | * | 12/2007 | Fallin et al. | 606/104 |
| 7,377,735 B2 | * | 5/2008 | Cosenza et al. | 411/517 |
| 2005/0049593 A1 | * | 3/2005 | Duong et al. | 606/69 |
| 2006/0064097 A1 | | 3/2006 | Bray | |
| 2006/0074421 A1 | * | 4/2006 | Bickley et al. | 606/72 |
| 2006/0276793 A1 | * | 12/2006 | Berry | 606/69 |
| 2009/0018662 A1 | | 1/2009 | Pasquet et al. | |
| 2009/0182383 A1 | * | 7/2009 | Prybyla et al. | 606/280 |
| 2009/0265007 A1 | | 10/2009 | Colleran | |
| 2010/0234895 A1 | | 9/2010 | Hess | |

FOREIGN PATENT DOCUMENTS

WO   WO 2007/014192   *   2/2007

* cited by examiner

*Primary Examiner* — Todd Manahan
*Assistant Examiner* — Jessica Weiss
(74) *Attorney, Agent, or Firm* — Edwards Wildman Palmer LLP; Joshua L. Jones (57) ABSTRACT

A screw fixation system includes a plate having opposed first and second surfaces, and a hole defined in the plate which extends between the first and second surface. A screw is included having a head and a shaft extending from the head and defining a longitudinal axis for the screw, the shaft of the screw being configured and adapted to be inserted into the hole. A retainer is circumferentially positioned around the shaft of the screw and proximate to the screw head. The retainer is configured to engage with the plate proximate the hole when the shaft of the screw has been inserted into the hole so as to resist removal of the screw from the hole and to allow removal of the screw from the hole when a preset torque is applied to the screw.

13 Claims, 13 Drawing Sheets

FIXATION PLATE SCREW RETENTION

CROSS-REFERENCE TO RELATED APPLICATIONS

This application claims the benefit of priority to U.S. Provisional Application No. 61/229,525, filed Jul. 29, 2009, which is hereby incorporated by reference in its entirety.

BACKGROUND OF THE INVENTION

1. Field of the Invention

The present invention relates to fixation plates. More particularly, the invention relates to controlling the backing out of screws from such fixation plates.

2. Description of Related Art

A wide variety of bone fixation plates exist. An exemplary plate carries a number of screws, each extending through an associated aperture in the plate and attached to bone. In the art of orthopedic fixation, it is now common for surgeons to utilize fixation plates for the treatment of spinal disorders which can include spinal anomalies, spinal injuries, disc conditions, and bone conditions.

While the procedure of implanting a bone fixation plate carries its own potential for complications, an added risk of complication is in the tendency of fixation screws to back out or loosen with respect to the remaining implant components. The loosening of the screws can lead to failure of the device. In the case of cervical spine fixation, for example, a loose screw could penetrate the esophagus causing infection.

The tendencies of screws to back out of plates has led to proposals for a wide variety of mechanisms for retaining screws against back-out. However, most of the systems employ some form of secondary locking screw. Such a secondary locking screw inherently increases the complexity and cost of the device while further increasing the implantation time. Also, these secondary locking screws themselves can loosen and back out of the plate over time.

Such conventional methods and systems have generally been considered satisfactory for their intended purpose. However, there is still a need in the art for an implant system that provides a fixation plate screw locking system that allows for improved prevention of fixation screws from backing out while having fixation screws that can still be removed from the implant device if necessary. There also remains a need in the art for such an implant system that is easy to make and use. The present invention provides a solution for these problems.

SUMMARY OF THE INVENTION

The subject invention is directed to a new and useful screw fixation system. The screw fixation system includes a plate having opposed first and second surfaces, and a hole defined in the plate which extends between the first and second surface. A screw is included having a head and a shaft extending from the head and defining a longitudinal axis for the screw, the shaft of the screw being configured and adapted to be inserted into the hole. A retainer is circumferentially positioned around the shaft of the screw and proximate to the screw head. The retainer is configured to engage with the plate proximate the hole when the shaft of the screw has been inserted into the hole so as to resist removal of the screw from the hole and to allow removal of the screw from the hole when a preset torque is applied to the screw.

In accordance with certain embodiments, the plate includes a plurality of holes and each hole receives a screw and a retainer associated therewith. The retainer can be a split ring to permit the retainer to radially compress when a preset torque is applied to the screw to allow insertion of the screw. The retainer can be a split ring with a vertical or diagonal slit to permit the retainer to radially compress when a preset torque is applied to the screw to allow removal of the screw. The retainer can have a substantially quadrilateral radial cross-section.

In certain embodiments, the shaft of the screw includes a circumferential channel which is configured to receive the retainer. The channel can include a bottom surface which is formed at an oblique angle with respect to the longitudinal axis of the screw, wherein the channel is configured to receive the retainer. The retainer can have an inner peripheral surface which is adapted to mate with the bottom surface of the channel when the retainer is radially compressed into the channel. At least one corner of the retainer can be rounded to facilitate engagement of the retainer in the channel. The bottom surface of the channel can be at an angle of about eight degrees to about fifteen degrees with respect to the longitudinal axis of the screw, wherein the channel is configured to receive the retainer. It is also contemplated that the bottom surface of the channel can be at an angle of about twelve degrees, or any other suitable angle, with respect to the longitudinal axis of the screw.

In accordance with certain embodiments, the plate includes a circumscribing undercut surface inset from the second surface of the plate formed about the hole to accommodate angled engagement of the screw. The screw shank can have a keyway and the retainer can have a corresponding key configured to engage the keyway and restrict relative rotation of the screw and retainer. The retainer can have a band portion and a plurality of lateral projections extending from the band portion wherein the plurality of projections are configured to engage a portion of the second surface of the plate adjacent the hole. The plate can include a circumscribing plurality of radially extending channels inset from the second surface of the plate adjacent to the hole and configured to engage lateral projections of the respective retainer.

The invention also provides a screw fixation system with a plurality of flexible radially inward extending petals in the plate. The plate has opposed first and second surfaces, and a hole defined in the plate which extends between the first surface and second surface. A plurality of flexible radially inward extending petals are circumferentially spaced apart from one another around the periphery of the hole. A screw having a head and a shaft extending from the head and defining a longitudinal axis is included. The shaft of the screw is configured and adapted to be inserted into the hole and to engage with the flexible petals, the flexible petals being configured to engage the screw to resist backing out of the screw from the plate.

These and other features of the systems and methods of the subject invention will become more readily apparent to those skilled in the art from the following detailed description of the preferred embodiments taken in conjunction with the drawings.

BRIEF DESCRIPTION OF THE DRAWINGS

So that those skilled in the art to which the subject invention appertains will readily understand how to make and use the devices and methods of the subject invention without undue experimentation, preferred embodiments thereof will be described in detail herein below with reference to certain figures, wherein.

DETAILED DESCRIPTION

Figure 1:
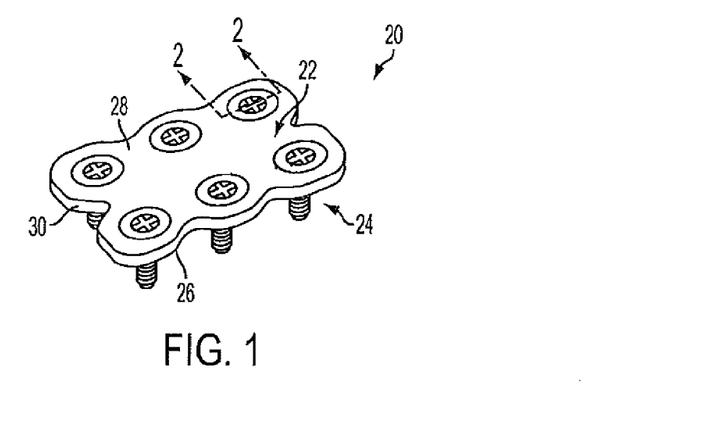
FIG. 1 is a perspective view of an exemplary embodiment of a fixation plate system constructed in accordance with the present invention, showing a plate with a plurality of screws seated in the plate.

Reference will now be made to the drawings wherein like reference numerals identify similar structural features or aspects of the subject invention. For purposes of explanation and illustration, and not limitation, a perspective view of an exemplary embodiment of a fixation plate system in accordance with the invention is shown in FIG. 1 and is designated generally by reference character 20. Other embodiments of fixation plate systems in accordance with the invention, or aspects thereof, are provided in FIGS. 2-14C, as will be described. The systems of the invention can be used to provide a fixation plate screw locking system that allows for improved prevention of fixation screws from backing out while having fixation screws that can still be removed from the plate if necessary, for example.

FIG. 1 shows a bone fixation plate assembly 20 including a plate 22 and a plurality of screws 24. The exemplary plate is formed as a unitary single metal piece having a second face 26 for contacting the bone(s) to be secured thereto and an opposite first face 28. A lateral perimeter 30 circumscribes the plate.

Figure 2:
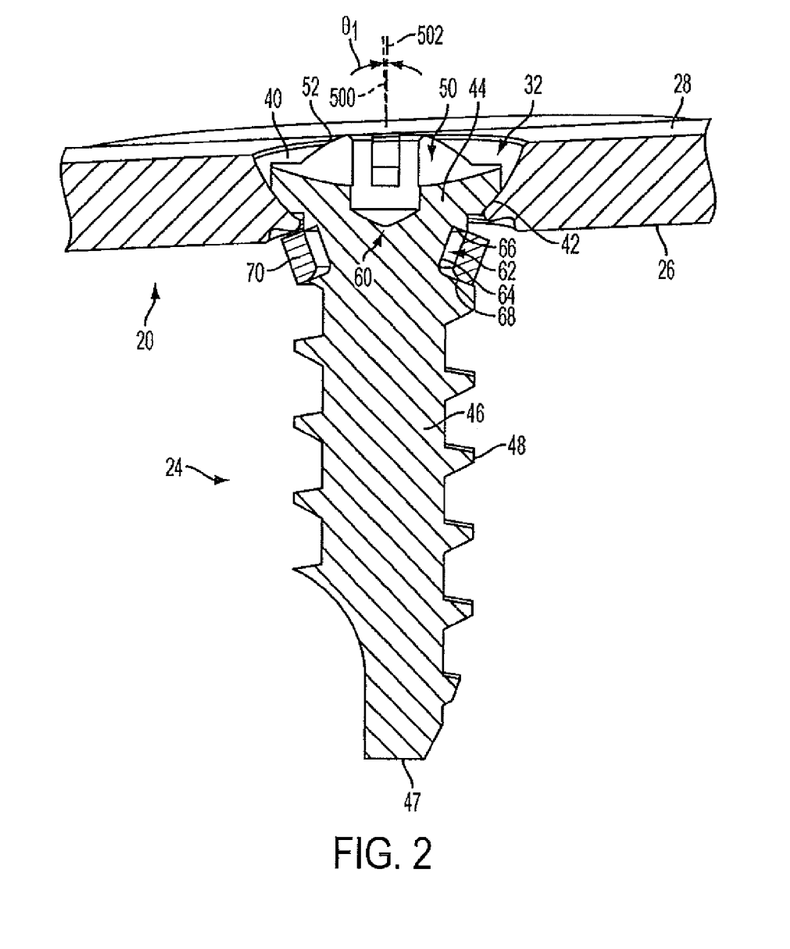
FIG. 2 is a cross-sectional side elevation view of the fixation plate system of FIG. 1, taken along line 2-2, showing a screw with a retainer seated in the plate.

Referring now to FIG. 2, each screw is accommodated by an associated hole (aperture) 32 in the plate. As is discussed further below, each hole 32 has a central axis 500. As is discussed further below, the axis 500 may coincide with the axis 502 of the screw with allowance for relative excursions. An exemplary angle between the axes 500 and 502 is shown as $\theta_1$. Hole 32 is bounded by a surface including a convex bowl/dish 40 divergently opening toward the first face 28. The bowl curvature is complementary to the curvature of a convex peripheral surface portion 42 of an underside of the screw head 44. A shank or shaft 46 depends from screw head 44. Shaft 46 extends from a proximal end near head 44 to a distal end or tip 47 and bears an external thread 48 for engaging the bone.

With screw 24 in an installed condition, the convex peripheral surface portion 42 may be in sliding engagement with the bowl 40 to accommodate orientational tolerance of screw 24 relative to plate 20. Tool-engaging features, e.g. facets 50, are formed in the upper surface 52 of head 44 for engaging a screwdriver, allan wrench, or other tool as may be known in the art or yet developed. In a transition region 60 between head 44 and shaft 46, screw 24 includes a radially inwardly directed channel 62 having a base 64, an upper side surface 66, and a lower side surface 68. As is discussed further below, channel 62 carries a split ring retainer 70. The exemplary retainer has an angular/diagonal (off-longitudinal) split 72, shown in FIG. 4.

Figure 3:
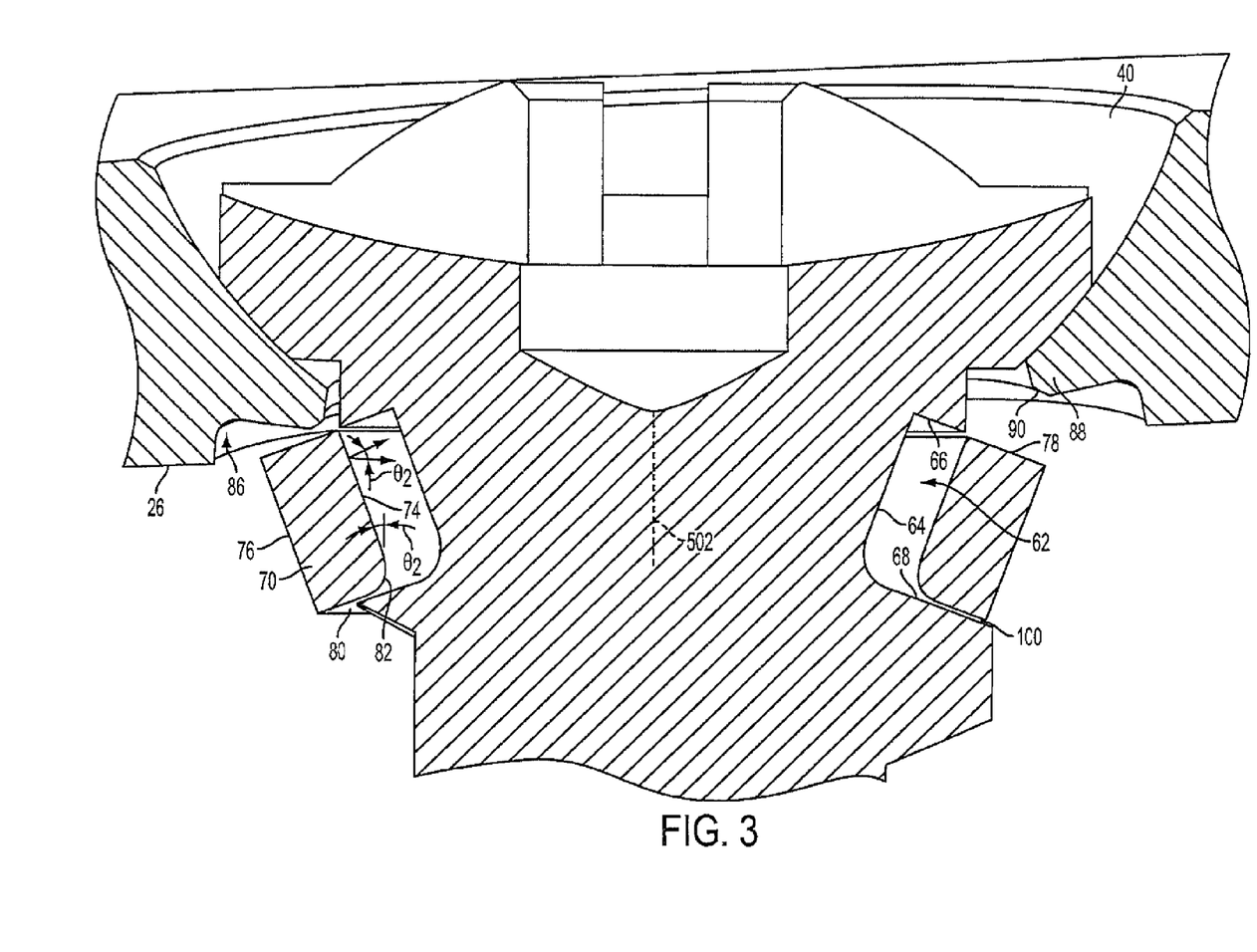
FIG. 3 is an enlarged view of a portion of the plate assembly of FIG. 2, showing the engagement of the retainer and screw seated in the plate.
Figure 4:
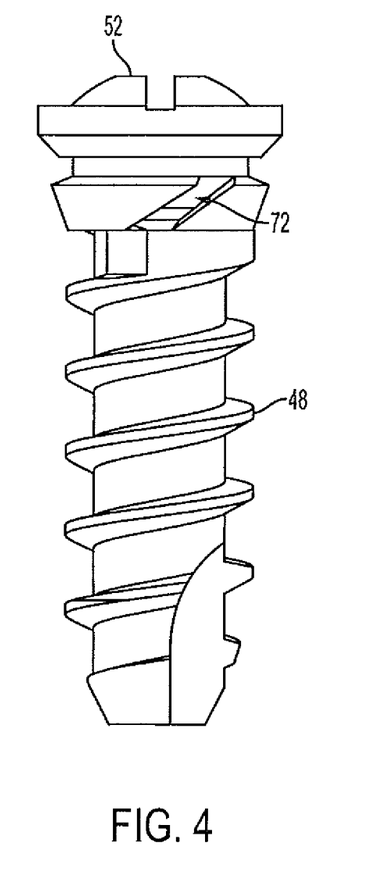
FIG. 4 is a side elevation view of a portion of the plate assembly of FIG. 2, showing the screw with a retainer split having a diagonal slit.

Referring now to FIG. 3, the exemplary retainer 70 has a radial cross-section characterized as a modified rectangle with inboard and outboard faces 74 and 76 along the longer legs of the rectangle and upper and lower rim faces 78 and 80 along the shorter legs of the rectangle. An optional rounded transition 82 is provided between the inboard face 74 and the lower rim face 80 to facilitate engagement of retainer 70 in channel 62. The shape of retainer 70 is essentially complementary to that of channel 62. The exemplary retainer 70 and channel 62 are oriented at an angle that is off-radial (i.e., the surface normals, channel base 64, and retainer inboard face 74 are off-radial by an angle $\theta_2$ (e.g., about 12°, more generally 8-15°. The surface normals of the channel sides and retainer rims are similarly off-longitudinal. Higher angles $\theta_2$ can be achieved by increasing the wall thickness of the retainer and making the groove in the screw deeper. Those skilled in the art will readily appreciate that any suitable angles can be used for channel 62 and retainer 70 without departing from the spirit and scope of the invention.

The exemplary hole 32 is further bounded by a circumscribing undercut 86 in second face 26, leaving an annular lip 88 between the undercut 86 and an adjacent portion of bowl

40. Undercut 86 may accommodate the retainer during angular excursions of screw 24 relative to plate 20.

In the installed condition, an initial backing out of screw 24 causes retainer upper rim face 78 to contact an adjacent portion, e.g., a bevel 90, of lip 88. With the lower rim face 80 of retainer 70 engaging lower side 68 of channel 62, further backing out is resisted. However, the off-radial angle of upper rim surface 66 may be selected to permit screw extraction provided that the backing out force reaches a sufficient level (e.g., associated with intentional unscrewing rather than incidental vibration). When the force reaches a sufficient amount, a camming action between retainer 70 and the surface bounding/defining holes 32 will tend to radially contract retainer 70, causing retainer 70 to snap outward through hole 32. The relatively shallow (near longitudinal) angle of the surface 76 provides relative ease of compression of retainer 70 during insertion. The more abrupt (radial) angle of surface 78 provides relatively higher resistance to spring compression during retraction and, thereby, relatively higher required extraction force. The variability of toggle between screw and plate installation/retraction forces required can also be varied by varying the tightness with which retainer 70 locks onto plate 22.

The components may first be manufactured, for example, via machining from appropriate metal stock, or by any other suitable process. Exemplary materials for the components of system 20 include appropriate implantable materials such as titanium, cobalt, Hastelloy (available from Haynes International of Kokomo, Ind.), nitinol, PEEK, and the like. Exemplary plate, screw, and retainer materials are medical grade titanium, titanium alloys, and the like. Those skilled in the are will readily appreciate that any suitable materials can be used without departing from the spirit and scope of the invention.

Figure 5:
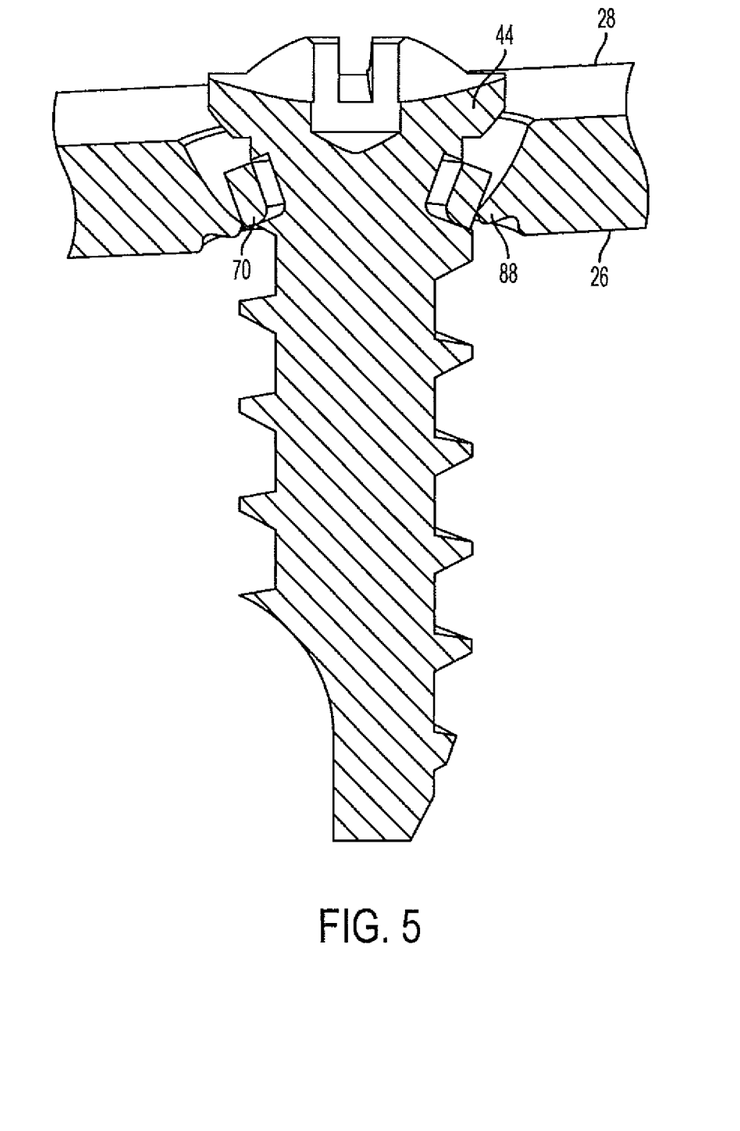
FIG. 5 is a cross-sectional side elevation view of the fixation plate of FIG. 1, showing the screw and retainer ring assembly during insertion into the plate.

The retainers may be assembled to their respective screws by inserting the screw tips through the retainers. A camming engagement between screw threads 48 and angled inboard face 74 of retainer 70 will expand retainer 70 allowing retainer 70 to be brought into alignment with channel 62 whereupon retainer 70 may relax into channel 62. Thereafter, each assembled screw/retainer may be inserted into the associated hole 32. Typically, plate 20 will have been prepositioned on the bone and pilot holes may have been drilled for screws 24. As each screw 24 is screwed into the bone, its retainer 70 will come into contact with bowl 40 (e.g., a junction 100 of outboard face 76 and lower rim face 80 contacting bowl 40). The shape of the bowl 40 may produce a caroming interaction contracting retainer 70, as shown in FIG. 5, and allowing retainer 70 to be snapped passed lip 88.

Figure 6:
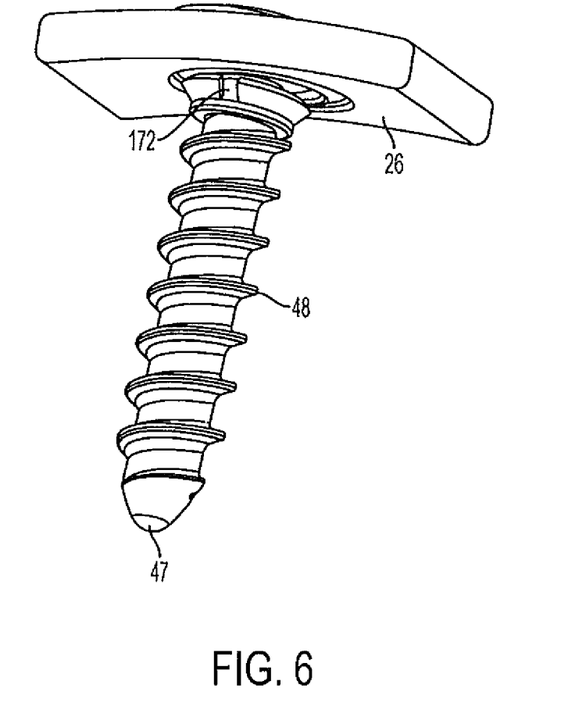
FIG. 6 is a perspective view of another exemplary embodiment of a fixation plate system constructed in accordance with the present invention, showing a screw with a split ring retainer having a vertical slit.

Further embodiments are shown and discussed below with only partial plates modeled (i.e., showing only one hole). However, the hole and screw/retainer configurations may be applied to single or multi-hole plates as described above or below. FIG. 6 shows a system similar to that of FIGS. 2-5 but wherein the ring is longitudinally split at slot 172 rather than diagonally split as described above.

Figure 7:
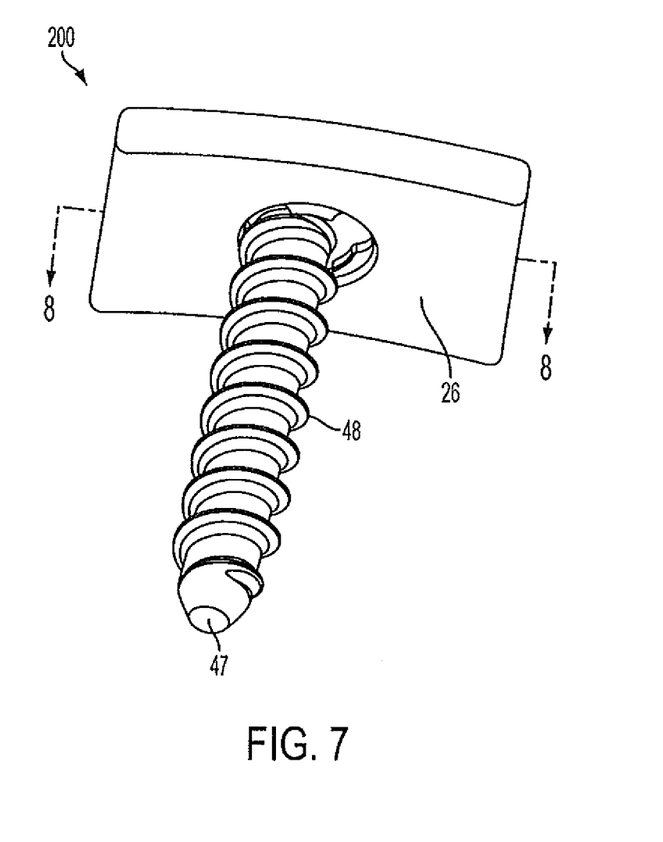
FIG. 7 is a perspective view of another exemplary embodiment of a fixation plate system constructed in accordance with the present invention, showing a plate with inward extending petals engaging a screw.
Figure 8:
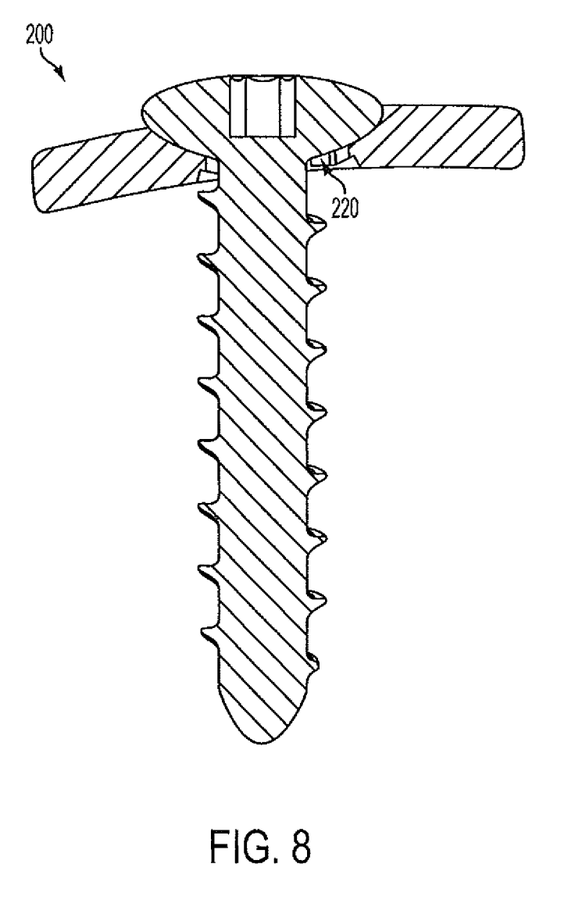
FIG. 8 is a cross-sectional elevation view of the screw and plate of FIG. 7, taken along line 8-8. showing a plate with petals engaging the screw.
Figure 9:
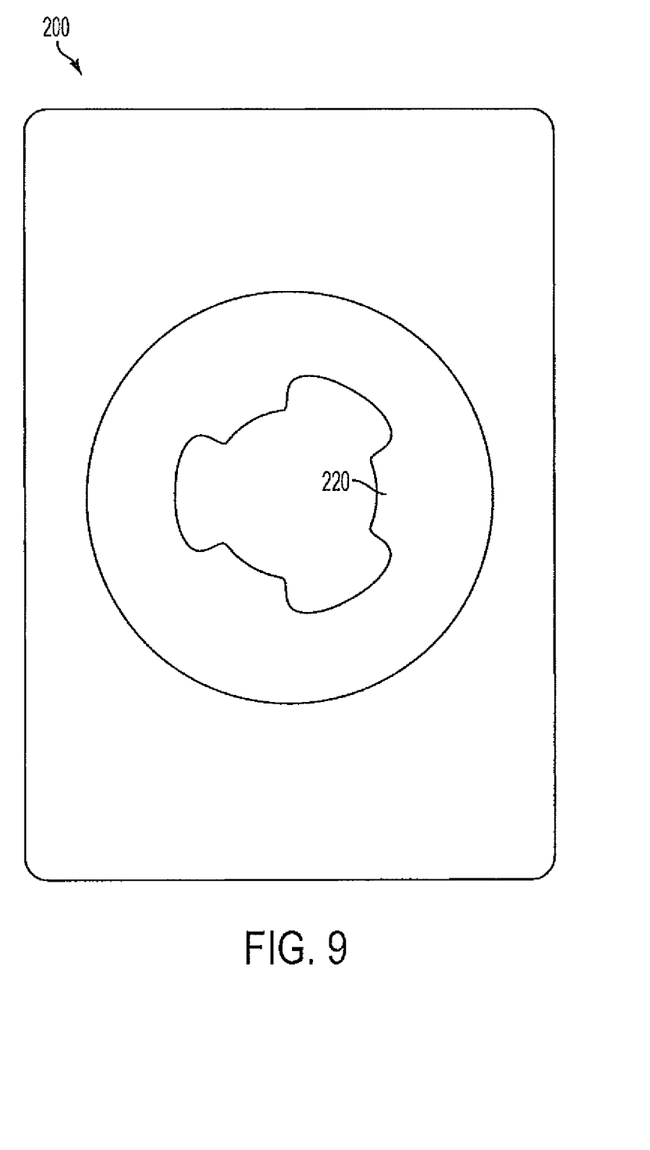
FIG. 9 is a plan view of the plate of FIG. 7, showing the petals of the plate with the screw removed.

FIGS. 7-9 show a retainer ring-less system 200 wherein the lip is segmented into individual, inwardly extending petals 220. Petals 220 can engage thread 48 to resist backing out. It is also possible to use such petals with a retainer ring such as those described herein. During insertion, petals 220 may flex to allow passing of the screw. An inward/downward (toward the bone surface) angle of the petals may cause relative ease of flexing upon insertion compared with backing out for extraction. Petals 220 are angled toward the tip of the screw and flex outward at insertion. At screw removal, petals 220 flex in the opposite direction but greater force is needed to flex them.

Figure 10:
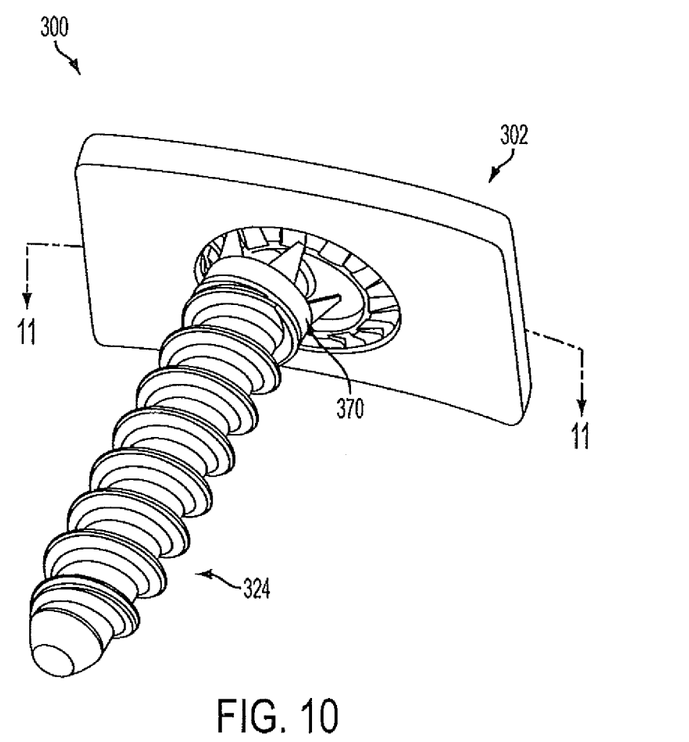
FIG. 10 is a perspective view of another exemplary embodiment of a fixation plate system constructed in accordance with the present invention, showing a plate and screw with a retainer and lateral projections from the retainer engaging the plate.
Figure 11:
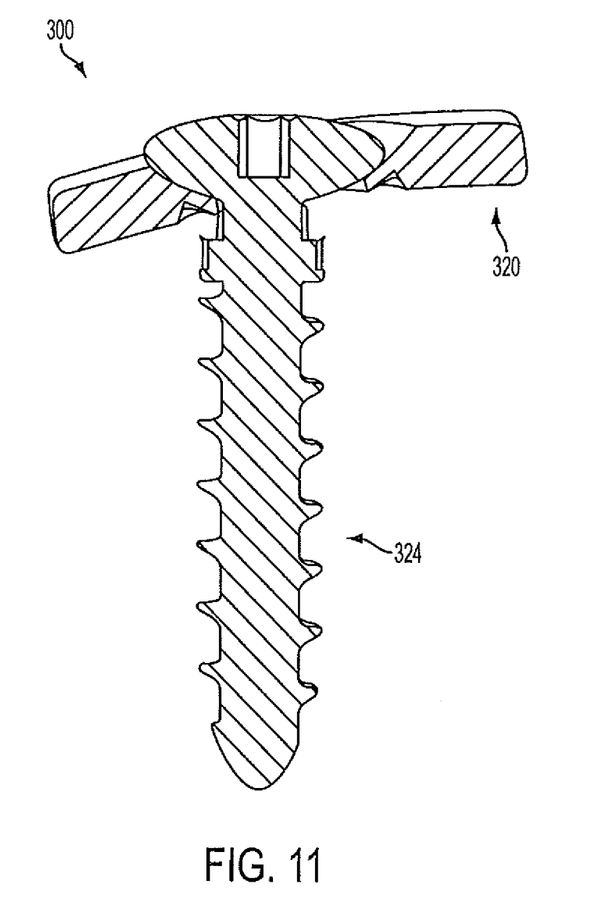
FIG. 11 is a cross-sectional elevation view of the fixation plate system of FIG. 10, taken along line 11-11, showing the plate and screw with the retainer removed.
Figure 12A:
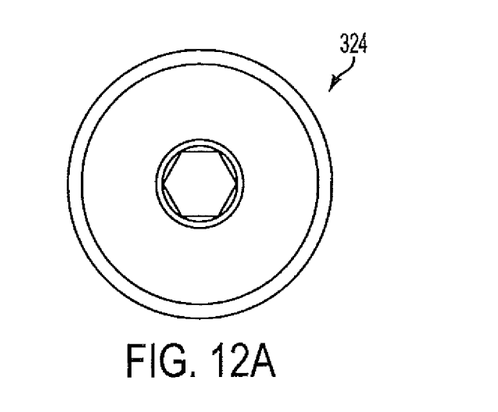
FIG. 12A is a plan view from above of the fixation plate system of FIG. 10, showing the heat of the screw.
Figure 12B:
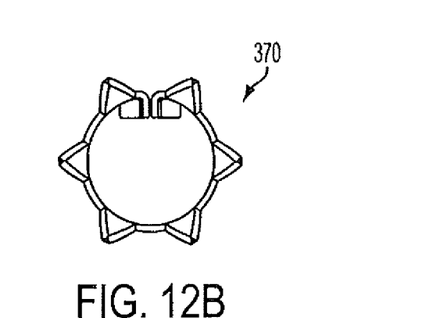
FIG. 12B is a plan view from above of a portion of the fixation plate system of FIG. 10, showing the retainer with lateral projections.
Figure 12C:
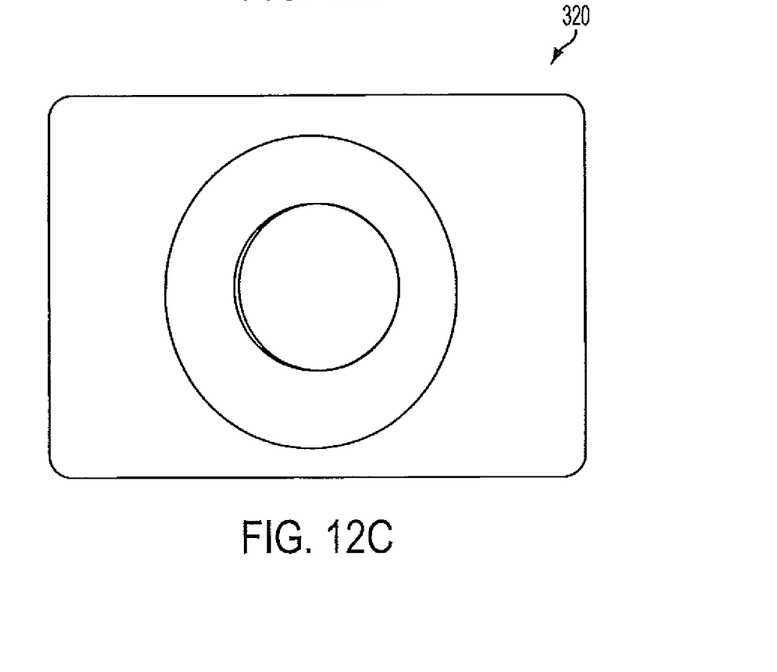
FIG. 12C is a perspective view from above of a portion of the fixation plate system of FIG. 10, showing the plate.
Figure 13A:
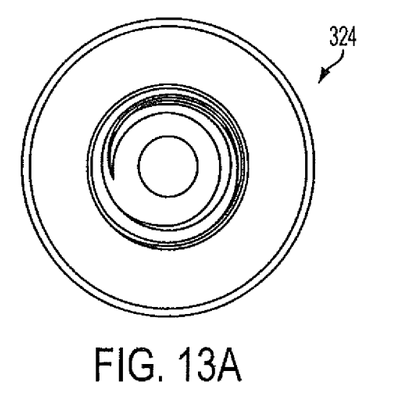
FIG. 13A is a plan view from below of a portion of the fixation plate system of FIG. 10, showing the screw.
Figure 13B:
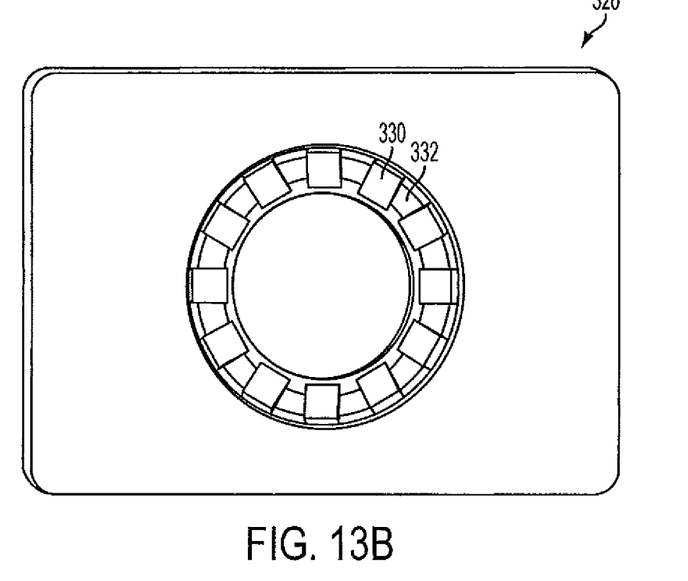
FIG. 13B is a perspective view from below of a portion of the fixation plate system of FIG. 10, showing the plate with a plurality of grooves circumscribing the hole.
Figure 13C:
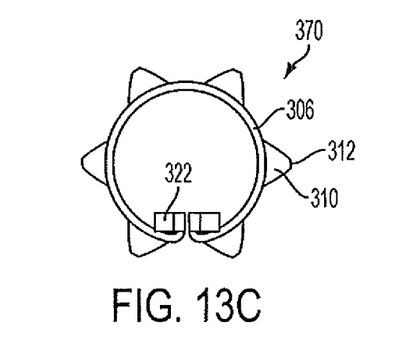
FIG. 13C is a plan view from below of a portion of the fixation plate system of FIG. 10, showing the retainer with lateral projections.
Figure 14A:
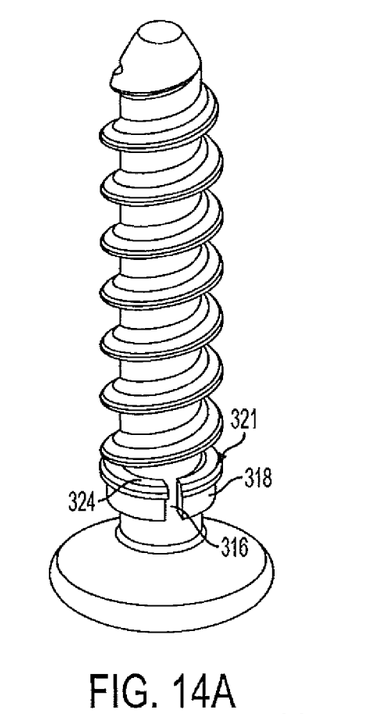
FIG. 14A is a perspective view of a portion of the fixation plate system of FIG. 10, showing the keyway of the screw.
Figure 14B:
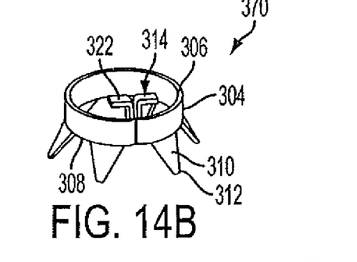
FIG. 14B is a perspective view of the fixation plate system of FIG. 10, showing the key of the retainer for engaging the keyway of the screw.
Figure 14C:
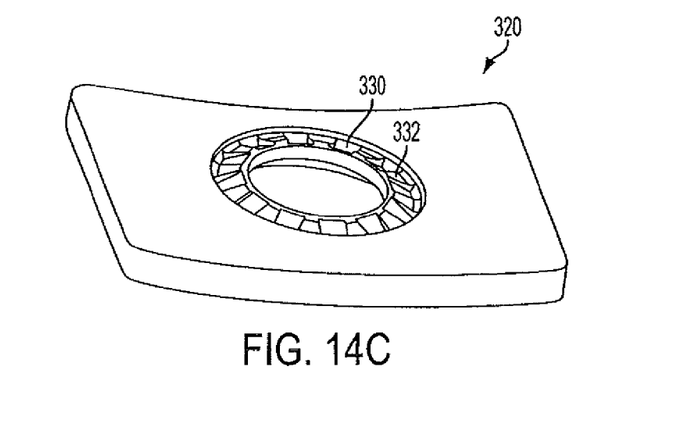
FIG. 14C is a perspective view of the fixation plate system of FIG. 10, showing the plate with a plurality of grooves circumscribing the hole for engaging the lateral projections of the retainer.

FIGS. 10-14C show a system having a crown-like retention ring 370. The crown may be formed of sheet metal (e.g., as a single piece) and having a wrapped band portion 304, as shown in FIG. 14B, having a lower rim 306 and an upper rim 308. A series of projections 310 extend upward and outward from the upper rim 308 to tips 312. A pair of ends of the band fold inward and are bent to form an inward extending key 314 which can fit into a longitudinal slot 316 along a boss 318 of screw 324 just below its head to resist or prevent relative rotation of screw 324 and retainer 370. Boss 318 includes a lower flange 320 which may engage surface 306 to longitudinally retain retainer 370 to screw 324. Bent end portions 322, shown in FIG. 13C, of key 314 can contact the underside 324 of flange 321 to resist relative upward longitudinal movement of retainer 370. The underside of the lip of plate 320 has a series of blind radial channels 330 separated by lands 332, as shown in FIGS. 10, 1311, and 14C. FIGS. 12A-12C, 13A-13C, and 14A-14C show screw 324, retainer 370, and plate 320 separately from above, below, and in perspective, respectively. In FIG. 11, the engagement of screw 324 with plate 320 is shown as in FIG. 10, but with retainer 370 removed for clarity.

Upon installation of the screw/retainer combination, projections 310 flex through the lip of plate 320 and become captured on the underside of the lip, as shown in FIG. 10. Cooperation of tips 312 with grooves 330 resists relative rotation of the screw/retainer assembly against plate 320. Similarly, cooperation of projections 310 with the underside of the lip resists longitudinal extraction. However, projections 310 may have sufficient flexibility, which can be elastic or inelastic, that a sufficient extraction force can bend projections 310 over onto the outer surface of band portion 304 and, thereby, allow extraction of the screw/retainer with sufficient extraction force (e.g., from intentional unscrewing).

The methods and systems of the present invention, as described above and shown in the drawings, provide for implant systems with superior properties including improved prevention of backing out of fixation screws. The methods and systems described herein allow for variability in the angle of the screw relative to the plate during its application. This is a distinct advantage over fixed locking plates which have a strict angle for attachment of the screws to the plate.

While the apparatus and methods of the subject invention have been shown and described with reference to preferred embodiments, those skilled in the art will readily appreciate that changes and/or modifications may be made thereto without departing from the spirit and scope of the subject invention.

What is claimed is:

1. A screw fixation system, comprising:
    a plate having opposed first and second surfaces, and a hole defined in the plate which extends between the first and second surfaces;
    a screw having a head and a shaft extending from the head and defining a longitudinal axis for the screw, the shaft of the screw being configured and adapted to be inserted into the hole; and
    a retainer circumferentially positioned around the shaft of the screw and proximate to the screw head, the retainer being configured to engage with the plate proximate the hole when the shaft of the screw has been inserted into the hole so as to resist removal of the screw from the hole, the retainer including an upper rim surface that is angled obliquely relative to the shaft of the screw, wherein the upper rim surface of the retainer and the hole of the plate are configured so that camming action between the upper rim surface and the plate contract the retainer to allow removal of the screw from the hole when a preset torque is applied to the screw and wherein the shaft of the screw includes a circumferential channel and the retainer is captive in the channel.

2. The system of claim 1, wherein the plate includes a plurality of holes and each hole receives a screw and a retainer associated therewith.

3. The system of claim 1, wherein the retainer is a split ring to permit the retainer to radially compress when a preset torque is applied to the screw to allow insertion of the screw.

4. The system of claim 3, wherein the retainer is a split ring with a diagonal slit to permit the retainer to radially compress when a preset torque is applied to the screw to allow removal of the screw.

5. The system of claim 1, wherein the retainer has a substantially quadrilateral radial cross-section.

6. The system of claim 1, wherein the channel includes a bottom surface which is formed at an oblique angle with respect to the longitudinal axis of the screw, wherein the channel is configured to receive the retainer.

7. The system of claim 6, wherein the retainer has an inner peripheral surface which is adapted to mate with the bottom surface of the channel when the retainer is radially compressed into the channel.

8. The system of claim 7, wherein at least one corner of the retainer is rounded to facilitate engagement of the retainer in the channel.

9. The system of claim 6, wherein the bottom surface of the channel is at an angle of eight degrees to fifteen degrees with respect to the longitudinal axis of the screw, wherein the channel is configured to receive the retainer.

10. The system of claim 9, wherein the bottom surface of the channel is at an angle of twelve degrees with respect to the longitudinal axis of the screw.

11. The system of claim 1, wherein the plate includes a circumscribing undercut surface inset from the second surface of the plate formed about the hole to accommodate angled engagement of the screw.

12. The system of claim 1, wherein the screw shaft has a keyway and the retainer has a corresponding key configured to engage the keyway and restrict relative rotation of the screw and retainer.

13. A bone fixation system, comprising:
a plate having opposed first and second surfaces, and a plurality of holes defined through the plate between the first surface and second surfaces;
a plurality of screws, each having a head and a shaft extending from the head and defining a longitudinal axis for the screw, the shaft of each of the plurality of screws being configured and adapted to be inserted into a respective hole; and
a plurality of retainers, each retainer being circumferentially seated around a respective one of the screws, each of the retainers being configured to engage with the plate proximate the hole at an angle of eight degrees to fifteen degrees with respect to the longitudinal axis of the screw when the shaft of the respective screw has been inserted into the respective hole so as to resist removal of the screw from the hole, each retainer including an upper rim surface that is angled obliquely relative to the shaft of the respective screw, wherein the upper rim surface of each retainer and the respective hole of the plate are configured so that camming action between the upper rim surface and the plate contract the retainer and to allow removal of the screw from the hole when a preset torque is applied to the screw and wherein the shaft of the screw includes a circumferential channel and the retainer is captive in the channel.

\* \* \* \* \*